(12) United States Patent
Molinier et al.

(10) Patent No.: US 7,199,273 B2
(45) Date of Patent: Apr. 3, 2007

(54) SELECTIVE HYDROGENATION OF ALKYNES AND/OR DIOLEFINS

(75) Inventors: Michel Molinier, Houston, TX (US); John Di-Yi Ou, Houston, TX (US); Michael A. Risch, Seabrook, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 514 days.

(21) Appl. No.: 10/721,046

(22) Filed: Nov. 24, 2003

(65) Prior Publication Data

US 2005/0113613 A1    May 26, 2005

(51) Int. Cl.
*B01J 31/00* (2006.01)
*C07C 7/163* (2006.01)

(52) U.S. Cl. .................. 585/258; 585/262; 502/167

(58) Field of Classification Search ............... 502/167; 585/258, 262
See application file for complete search history.

(56) References Cited

U.S. PATENT DOCUMENTS

| | | | |
|---|---|---|---|
| 3,651,167 A | | 3/1972 | Rosset |
| 3,793,232 A | | 2/1974 | Duhaut et al. |
| 3,859,377 A | | 1/1975 | Gross et al. |
| 4,149,961 A | | 4/1979 | Antos |
| 4,207,169 A | | 6/1980 | Courty et al. |
| 4,243,516 A | | 1/1981 | Martino et al. |
| 4,420,420 A | | 12/1983 | Mita et al. |
| 4,487,848 A | | 12/1984 | Robinson et al. |
| 4,522,935 A | | 6/1985 | Robinson et al. |
| 4,677,094 A | | 6/1987 | Moser et al. |
| 4,691,070 A | | 9/1987 | Nakamura et al. |
| 4,705,906 A | * | 11/1987 | Brophy et al. ............. 585/262 |
| 5,233,118 A | | 8/1993 | Bricker et al. |
| 5,356,851 A | | 10/1994 | Sarrazin et al. |
| 5,364,998 A | | 11/1994 | Sarrazin et al. ............. 585/259 |
| 5,536,695 A | | 7/1996 | Blejean et al. |
| 5,877,363 A | | 3/1999 | Gildert et al. ............. 585/260 |
| 5,965,481 A | | 10/1999 | Durand et al. |
| 6,084,140 A | | 7/2000 | Kitamura et al. ........... 585/260 |
| 6,096,933 A | | 8/2000 | Cheung et al. |
| 6,153,090 A | | 11/2000 | Le Peltier et al. |
| 6,187,985 B1 | | 2/2001 | Le Peltier et al. |
| 6,255,548 B1 | | 7/2001 | Didillon et al. ............. 585/259 |
| 6,355,854 B1 | | 3/2002 | Liu |
| 6,436,871 B1 | | 8/2002 | Liu |
| 6,498,280 B1 | | 12/2002 | Uzio et al. |
| 6,503,866 B1 | | 1/2003 | Shepherd et al. |
| 6,514,904 B1 | | 2/2003 | Moser et al. |
| 6,586,647 B1 | | 7/2003 | Abrevaya et al. |
| 6,777,371 B2 | | 8/2004 | Liu |
| 2002/0068843 A1 | | 6/2002 | Dai et al. ................... 585/260 |
| 2002/0136686 A1 | | 9/2002 | Takahashi |

FOREIGN PATENT DOCUMENTS

| | | |
|---|---|---|
| WO | WO 98/47617 | 10/1998 |
| WO | WO 98/47618 | 10/1998 |
| WO | WO 98/47620 | 10/1998 |
| WO | WO 2004/046076 | 6/2004 |

OTHER PUBLICATIONS

Hydrazine From Wikipedia, the Free Encyclopedia, May 14, 2006.*
Li, et al., "Selective Catalytic Reduction of NO Over Metal Oxide or Noble Metal-Doped $In_2O_3/Al_2O_3$ Catalysts By Propene in the Presence of Oxygen", Reaction Kinetics and Catalysis Letters, 2003, vol. 80, No. 1, pp. 75-80, XP008030692.
U.S. Appl. No. 10/720,558, filed Nov. 24, 2003, Lowe et al.
U.S. Appl. No. 10/720,617, filed Nov. 24, 2003, Lowe et al.
U.S. Appl. No. 10/720,607, filed Nov. 24, 2003, Lowe et al.
H. Scott Fogler, *Elements of Chemical Reaction Engineering*, 2nd Edition, PTR Prentice Hall, Inc., pp. 29-52 (1992).
J. M. Smith, *Chemical Engineering Kinetics*, McGraw-Hill Book Company, pp. 231-279 (1956).
S. Asplund, "Coke Formation and Its Effect on Internal Mass Transfer and Selectivity in Pd-Catalysed Acetylene Hydrogenation", Journal of Catalysis, vol. 158, pp. 267-278 (1996).

* cited by examiner

*Primary Examiner*—Glenn Caldarola
*Assistant Examiner*—Prem C. Singh

(57) ABSTRACT

A process for selectively removing alkynes and/or diolefins from a feedstock also containing olefins comprises contacting the feedstock with hydrogen in the presence of a catalyst composition. The catalyst composition comprises at least one metal component selected from Groups 8 to 10 of the Periodic Table of Elements impregnated on a support, wherein an organic nitrogen-containing compound is contacted with the support before, during or after the metal impregnation.

18 Claims, No Drawings

SELECTIVE HYDROGENATION OF ALKYNES AND/OR DIOLEFINS

FIELD

This invention relates to a process for the selective hydrogenation of alkynes and/or diolefins to olefins.

BACKGROUND

Light olefins, such as ethylene, propylene and butylenes, can be produced using various processes such as steam cracking, fluid catalytic cracking, conversion of methanol to olefins, paraffin dehydrogenation, alcohol dehydration, methane coupling and Fischer Tropsch reactions. However, these processes often produce varying levels of acetylenic and/or diene by-products, such as acetylene, methyl acetylene (MA), propadiene (PD), butyne and butadiene. These by-products must be removed from the light olefin streams because they can act as poisons to the downstream processing catalysts, such as polymerization catalysts.

The preferred method of removing these by-products is by selective catalytic hydrogenation in which, for example, acetylene is converted to ethylene, methyl acetyene and propadiene are converted to propylene, and butyne and butadiene are converted to butylenes. Possible competing reactions include the oligomerization of two or more alkyne or diolefin molecules to produce heavier unsaturated compounds (generally referred to as "green oil") and the generation of saturates (for example, ethane, propane and butanes) as a result of over-hydrogenation. Both of these reactions are undesirable in that they reduce the selectivity to the required light olefins. However, the green oil is particularly problematic in that it decreases the life of the hydrogenation catalyst.

Currently, the catalysts proposed for this selective hydrogenation comprise at least one Group 8–10 metal, such as palladium or rhodium, often in combination with other metals, such as indium, wherein the metals are dispersed on a support, such as alumina. However, the activity and selectivity of such catalysts are normally dependent not only on the type of metal(s) employed but also on the ability to disperse or alloy small particles of the desired metal(s) homogeneously on the support. Typically supported metal catalysts are prepared by impregnation of the support with solutions containing salts of the desired metals, followed by drying and calcination. However, impregnation, and particularly slurry impregnation, can lead to non-homogeneous metal dispersion or alloying, particularly at high metal loadings.

There is therefore a need for an improved method of dispersing/alloying metals on a catalyst support such that the resultant catalyst exhibits improved performance in the selective hydrogenation of alkynes and/or diolefins.

U.S. patent application Publication No. 2002/0068843 discloses a catalyst for selectively hydrogenating acetylenic and diolefinic compounds with low green oil formation, the catalyst comprising the following active components loaded on a porous inorganic support: (1) at least one of platinum, palladium, nickel, ruthenium, cobalt, and rhodium; (2) at least one of silver, copper, zinc, potassium, sodium, magnesium, calcium, beryllium, tin, lead, strontium, barium, radium, iron, manganese, zirconium, molybdenum, and germanium; (3) at least one rare earth metal selected from scandium, yttrium and Lanthanides in Group IIIB of Periodic Table of Elements; and (4) bismuth. Preferably, component (1) is platinum or palladium component (2) is silver, potassium or sodium and component (3) is lanthanum or neodymium.

U.S. Pat. No. 6,255,548 discloses a method for selectively hydrogenating a feed comprising an acetylenic compound and/or a diolefin in the presence of a catalyst comprising at least one support, at least one Group VIII metal selected from nickel, palladium, platinum, rhodium, ruthenium and iridium and at least one additional element M selected from germanium, tin, lead, rhenium, gallium, indium, thallium, gold, and silver, wherein the catalyst is formed by impregnating the support with an aqueous solution containing at least one water-soluble organometallic compound of said element M comprising at least one carbon-M bond. The preferred Group VIII metals are nickel, palladium and platinum and the preferred additional elements M are germanium, tin, gold, and silver.

U.S. Pat. No. 5,877,363 discloses a process for the removal of acetylenes and 1,2-butadiene from a $C_4$ aliphatic hydrocarbon stream by contacting the hydrocarbon stream with hydrogen in a distillation column reactor containing a bed of hydrogenation catalyst comprising a Group VIII metal selected from platinum, palladium, rhodium or mixtures thereof; optionally in combination with a Group IB or Group VIB metal, and fractionally distilling the reaction mixture to remove a heavier fraction and removing a fraction overhead comprising substantially all of the $C_4$ compounds having reduced acetylenes and 1,2-butadiene content. The preferred hydrogenation catalyst is palladium.

U.S. Pat. Nos. 5,356,851 and 5,364,998 disclose a catalyst and a process for the selective hydrogenation of unsaturated compounds, wherein the catalyst contains 0.1 to 10% of at least one Group VIII metal selected from nickel, palladium, platinum, rhodium and ruthenium and 0.01 to 10% of at least one Group IIIA metal selected from gallium and indium. The molar ratio of Group IIIA metal to Group VIII metal is between 0.2 and 5, preferably between 0.3 and 2. The metals are deposited on a catalyst support by (a) impregnating the support with a solution of a Group IIIA metal compound precursor, then (b) impregnating the product of (a) with a solution of a Group VIII metal compound and then (c) calcining the product of (b) at 110 to 600° C. The preferred Group VIII metals are nickel, palladium and platinum.

Published International Application No. WO 98/47618 discloses a process for producing a Fischer-Tropsch catalyst wherein a multi-functional carboxylic acid having 3 to 6 carbon atoms is used to impregnate and disperse a rhenium compound and a compound of a catalytic metal, such as copper or iron, onto a refractory oxide support, such as titania. Published International Application Nos. WO 98/47617 and WO 98/47620 disclose similar processes but in which the dispersion aids are a polyol and a carbohydrate or sugar respectively.

United Kingdom Patent Application No. 0227086.6 (Attorney Docket No. 01CL123), filed Nov. 20, 2002, discloses a method for preparing a metal supported catalyst in which metal dispersion is improved by forming an organic complex of at least one catalytically active metal during manufacture of the catalyst and then partially or fully decomposing the complex before reduction of the metal with hydrogen. The catalyst is said to be useful in catalyzing Fischer-Tropsch reactions and in removing organosulfur compounds from hydrocarbon streams. There is no disclosure of use of the catalyst in the selective hydrogenation of alkynes and/or diolefins.

Co-pending U.S. patent application Ser. No. 10/720,617 filed Nov. 24, 2003, describes a catalyst and process for selectively hydrogenating alkynes and/or diolefins, wherein the catalyst comprises a support, a rhodium component present in an amount such that the catalyst composition comprises less than 3.0% of rhodium by weight of the total catalyst composition; and an indium component present in an amount such that the catalyst composition comprises at least 0.4% and less than 5.0% of indium by weight of the total catalyst composition. The rhodium and indium components can be added to the support by impregnation or co-precipitation.

Co-pending U.S. patent application Ser. No. 10/720,558 filed Nov. 24, 2003, describes a catalyst and process for selectively hydrogenating alkynes and/or diolefins, wherein the catalyst comprises at least two different metal components selected from Groups 8 to 10 of the Periodic Table of Elements and at least one metal component selected from Group 13 of the Periodic Table of Elements. The metal components can be added to the support by impregnation or co-precipitation.

SUMMARY

In one aspect, the present invention resides in a process for selectively removing alkynes and/or diolefins from a feedstock also containing olefins, the process comprising contacting the feedstock with hydrogen in the presence of a catalyst composition comprising a support and at least one metal component selected from Groups 8 to 10 of the Periodic Table of Elements, wherein the catalyst composition is produced by a method comprising:

(a) impregnating the support with a compound of said at least one metal;

(b) contacting said support with at least one organic nitrogen-containing compound; and (c) after (a) and (b), calcining the support.

Contacting of said support with said at least one organic compound can be effected before, after, and/or concurrently with impregnation of the support with a compound of said at least one metal.

In one embodiment, said at least one metal selected from Groups 8 to 10 of the Periodic Table of Elements includes rhodium.

Conveniently, the catalyst composition further comprises at least one metal component selected from Group 13 of the Periodic Table of Elements, such as indium.

Conveniently, the catalyst includes at least one additional metal component different from rhodium and selected from Groups 8 to 10 of the Periodic Table of Elements, such as iron, ruthenium or cobalt.

Conveniently, the organic nitrogen-containing compound is an aminoacid or aminoalcohol, for example 2-amino-2-methyl-1-propanol.

In another aspect, the present invention resides in a method of making a catalyst composition comprising a support, a first metal component comprising rhodium and a second metal component comprising at least one metal selected from Group 13 of the Periodic Table of Elements, wherein the method comprises (a) impregnating the support with a rhodium compound;

(b) impregnating the support with a compound of said second metal;

(c) contacting said support with at least one organic nitrogen-containing compound; and (d) calcining the support.

DETAILED DESCRIPTION OF THE EMBODIMENTS

The present invention relates to a process for selectively removing alkynes and/or diolefins from a feedstock also containing olefins by contacting the feedstock with hydrogen in the presence of a catalyst composition comprising a support which has been impregnated with a compound of at least one metal selected from Groups 8 to 10 of the Periodic Table of Elements and which has also been contacted with at least one organic nitrogen-containing compound. Contacting the support with an organonitrogen compound, such as an aminoacid or aminoalcohol, preferably an aminoalcohol, before, during or after the metal impregnation step is found to enhance the activity and/or olefin selectivity of the resultant catalyst.

The Periodic Table of Elements referred to herein is the IUPAC version described in the *CRC Handbook of Chemistry and Physics,* 78th Edition, CRC Press, Boca Raton, Fla. (1997).

Catalyst Composition

The present catalyst composition comprises at least one metal component selected from Groups 8 to 10 of the Periodic Table of Elements combined with a binder and/or a support. The term "component" is used to include a metal compound that may not be purely the elemental metal, but could, for example, be at least partly in another form, such as an oxide, hydride or sulfide form.

The at least one metal from Groups 8 to 10 of the Periodic Table of Elements is conveniently selected from platinum, palladium, rhodium, silver, iron, cobalt and ruthenium, with rhodium being preferred. More than one metal from Groups 8 to 10 of the Periodic Table of Elements can be present in the catalyst composition so that, for example, catalyst composition can conveniently contain two Group 8 to 10 metals. In addition, the catalyst composition can contain one or more metal components selected from Groups 1 to 7 and 11 to 15, and especially from Group 13, of the Periodic Table of Elements.

In one embodiment, the catalyst composition is a bimetallic catalyst including rhodium and indium as the active components. In such a case, the catalyst composition conveniently comprises from about 0.01% to about 10%, for example from about 0.1% to about 3.0%, such as from about 0.25% to about 2.5%, generally from about 0.3% to about 1.5%, of rhodium by weight of the total catalyst composition; and from about 0.01% to about 20%, for example from about 0.4% to about 5.0%, such as from about 0.5% to about 4.0%, generally from about 1.0% to about 3.0%, of indium by weight of the total catalyst composition.

In a further embodiment, the catalyst composition includes:

(a) a first component including a metal selected from Groups 8 to 10 of the Periodic Table of Elements, normally rhodium;

(b) a second component including a metal selected from Group 13 of the Periodic Table of Elements, normally indium; and (c) a third component comprising at least one metal different from said first and second components and selected from Groups 1 to 15, such as from Groups 8 to 10, of the Periodic Table of Elements, normally iron, cobalt and/or ruthenium.

In the further embodiment, the catalyst composition conveniently comprises from about 0.01% to about 20%, such as from about 0.04% to about 5%, by weight of the first component metal by weight of the total catalyst composition. In addition, the catalyst composition conveniently comprises from about 0.01% to about 30%, such as from about 0.05% to about 20%, by weight of the second component metal by weight of the total catalyst composition and from about 0.01% to about 50%, such as from about 0.05% to about 30%, by weight of the third component metal by weight of the total catalyst composition.

In addition to the active metal components discussed above, the catalyst composition also includes a support or binder material. Suitable support materials comprise amorphous inorganic oxides, such as clays, zirconia, alumina, silica, silica-alumina, ceria-alumina, aluminates (such as aluminates of Groups 1 and 2 and of the Periodic Table of Elements), aluminophosphates, magnesium silicate and magnesium oxide-silicon oxide mixtures, crystalline inorganic oxides, such as spinels, perovskites, and molecular sieves, and other solid inorganic materials, such as carbon, silicon nitride, silicon carbide, boron nitride and metal alloys. Preferred support materials include zirconia, alumina and ceria-alumina. The binder or support material conveniently comprises from about 50 wt % to about 99.9 wt %, such as from about 65 wt % to about 99.5 wt %, of the entire catalyst composition.

It is to be appreciated that all weight percentages for the metal components of the catalyst composition are based on the amount of elemental metal present by weight of the total catalyst composition including the binder or support.

Each of the active metal components may be substantially uniformly distributed throughout the support, can be located within a thin layer at the support surface (commonly referred to as eggshell), can be located at the center of the support (commonly referred to as eggyolk), or can be concentrated between the outer edge and the center of the support (commonly referred to as eggwhite). Preferably, the metal components are concentrated in a thin layer (not more than 1000 microns, conveniently not more than 500 microns, such as not more than 300 microns, for example not more than 100 microns deep) on the surface of the support.

Method of Making the Catalyst Composition

The catalyst composition of the invention is prepared by deposition of the catalytic metal, or metals, on a powder, or a previously pilled, pelleted, beaded, extruded, spray dried, or sieved support material by impregnation. In preparing the catalyst, the metals are deposited from solution on the support in preselected amounts to provide the desired absolute amounts, and weight ratios of the metals being deposited. Where the catalyst composition contains more than one metal, the individual metals can be deposited from solution onto the support in sequence, or can be codeposited from the same impregnating solution. The impregnating solution contains a compound (such as a nitrate, sulfate, halide, formate, acetate, citrate, oxoacetate, oxalate and acetylacetonate) of the chosen metal or metals in a suitable solvent, typically water. The volume of impregnating solution used in the impregnation usually ranges from about 0.25 to about 200 times the volume of the support.

In one embodiment, the impregnation is carried out by the incipient wetness technique, wherein the volume of the impregnating solution and amount of metals are predetermined to correspond to the maximum volume which will just fill the internal pore volume of the support, with no liquid in excess after impregnation of the support. Alternatively, slurry impregnation can be employed in which a solution containing the desired metal or metals is mixed with a slurry of the particulate support in a liquid, typically water, and the mixture is heated to drive off some or all of the liquid. As a further alternative, impregnation can be achieved by spraying a solution containing one or more metal compounds onto the support.

In accordance with the invention, in addition to the impregnation with the desired catalytic metals, the catalyst support is contacted with a nitrogen-containing organic compound, such as an aminoacid or aminoalcohol. Particularly suitable organonitrogen compounds are aminoalcohols, such as 2-amino-2-methyl-1-propanol. The organonitrogen compound is contacted with the support either before, during and/or after impregnation of the support with the metal compound(s). For example, when the catalyst composition includes rhodium and a Group 13 metal, such as indium, an organonitrogen compound can advantageously be present during impregnation of the support with a solution or solutions containing a rhodium compound and a Group 13 metal compound.

After impregnation, the catalyst composition is dried, suitably at temperatures ranging from about 25° C. to about 120° C., in an air, nitrogen or other gas stream or under vacuum. Thereafter, the catalyst composition is calcined at temperature ranging from about 100° C. to about 650° C., such as from about 110° C. to about 600° C. to convert the metal compounds to the elemental or an oxide form and to remove any remaining organonitrogen compound. Typically the calcination is conducted in an oxidizing atmosphere, such as air, or in an inert atmosphere, such as nitrogen. Alternatively, the calcination can be conducted in a reducing atmosphere, such as an atmosphere containing about 5 to about 30 mol % hydrogen, with the remainder being an inert gas, such as nitrogen, typically at a temperature of about 200° C. to about 500° C. In one practical embodiment, the catalyst composition is initially calcined in an oxidizing or inert atmosphere and then undergoes a further calcination in a reducing atmosphere.

Hydrogenation Process

The catalyst composition of the invention is capable of hydrogenating alkynes and/or diolefins in a feedstock that also contains olefins with high selectivity to olefins and low selectivity to green oil (alkyne and diolefin oligomers) and saturates. In particular, when used to selectively hydrogenate $C_2$ to $C_4$ alkynes and/or diolefins in a feedstock also containing $C_2$ to $C_4$ olefins, the present catalyst composition typically achieves an alkyne conversion in excess of 80%, such as in excess of 90%, with an olefin selectivity in excess of 50%, such as in excess of 60%, and a green oil selectivity of less than 10%, such as less than 8%. The reduction in green oil formation should also result in an extension of catalyst lifetime and/or operating cycle.

The selective hydrogenation of acetylene, methyl acetylene (MA), propadiene (PD), and/or butadiene (BD) is typically carried out in one of four unit types:

(a) Front-End Selective Catalytic Hydrogenation Reactors, where the feed is composed of $C_3$ and lighter hydrocarbons, or $C_2$ and lighter hydrocarbons. In the case of raw gas applications, other components such as butadiene, ethyl acetylene, dimethyl acetylene, vinyl acetylene, cyclopentadiene, benzene, and toluene can also be present.

(b) Back-End Selective Catalytic Hydrogenation Reactors, where the feed is composed of an ethylene-rich stream.

(c) MAPD Selective Catalytic Hydrogenation Reactors, where the feed is composed of a propylene-rich stream.

(d) BD Selective Catalytic Hydrogenation Reactors, where the feed is composed of a butylene-rich stream.

The operating parameters of an alkyne/alkadiene selective hydrogenation process are not narrowly critical and can controlled in view of a number of interrelated factors including, but not necessarily limited to, the chemical composition of the feedstock, the control systems and design of a particular plant, etc (i.e. different reactor configurations including front-end, tail-end, MAPD, and BD converters as mentioned briefly above). In general, however, suitable operating parameters include a temperature of from about 20° C. to about 150° C., such as from about 30° C. to about 100° C., a pressure of from about 690 kPa to 4100 kPa, such as from about 1400 kPa to 3400 kPa, a $H_2/C_2H_2$ molar feed ratio of from about 1 to about 1000, such as of from about 1.1 to about 800 and, assuming the reaction is in the vapor phase, a GHSV from about 100 to about 20,000, such as from about 500 to about 15,000 or, if the reaction is in the liquid phase, an LHSV of 0.1 to 100, such as from 1 to 25.

The following descriptions serve to illustrate how the inventive process may be practiced in the different commercial units.

In the case of a front-end (FE) selective hydrogenation reactor, the inlet operating temperature may range from about 30 to about 150° C., such as from about 50 to about 100° C. Representative operating pressures may range from about 100 psig to about 500 psig (about 690 to 3,500 kPa), such as from about 200 psig to about 400 psig (about 1400 to 2800 kPa). The GHSV may range from about 5000 to about 20,000, such as from about 8000 to about 15,000. Further, the $H_2$ partial pressure may range from about 25 psig to about 175 psig (about 172 to 1200 kPa), such as from about 50 psig to about 140 psig (about 345 to 965 kPa). The feedstreams in FE selective hydrogenation processes typically contain at least about 20% ethylene, and less than 1% acetylene, with the balance comprising ethane, methane, hydrogen and small amounts of similarly light components. (All percentages are mole % unless otherwise noted). Depending upon the process configuration of the plant, this feed stream can also contain $C_3$ components such as methyl acetylene, propadiene, propylene, and propane. Still heavier components such as 1,3 butadiene; 1,2 butadiene; ethyl acetylene; dimethyl acetylene; vinyl acetylene; cyclopentadiene; benzene; toluene and mixtures thereof may also be present as a result of certain process configurations.

In the case of a back-end selective hydrogenation reactor, the inlet operating temperature may range from about 30 to about 150° C., such as from about 40 to about 90° C. Representative operating pressures may range from about 100 psig to about 500 psig (about 690 to 3,500 kPa), such as from about 200 psig to about 400 psig (about 1400 to 2800 kPa). The GHSV may range from about 1000 to about 10,000, such as from about 3000 to about 8000. Further, the $H_2/C_2H_2$ molar feed ratio may range from about 0.5 to about 20, such as from about 1.0 to about 1.5. The feedstreams in back-end selective hydrogenation processes in may contain about 2% acetylene, about 70% ethylene, and the balance other $C_2$ compounds.

In the case of a methyl acetylene/propadiene (MAPD) selective hydrogenation reactor, operation can be conducted in either the liquid or vapor phase. In the case of liquid phase operation, the inlet operating temperature may range from about 20 to about 100° C., such as from about 30 to about 80° C. Representative operating pressures may range from about 150 psig to about 600 psig (about 1000 to 4100 kPa), such as from about 250 psig to about 500 psig (about 1700 to 3400 kPa). The LHSV may range from about 0.1 to about 100, such as from about 1 to about 10. In the case of the vapor phase operation, the inlet operating temperature may range from about 20 to about 600° C., such as from about 200 to about 400° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, such as from about 1 to about 10. The feedstreams in MAPD selective hydrogenation processes may contain at least 80% propylene, and less than 10% of a compound selected from the group consisting of methyl acetylene, propadiene, and mixtures thereof.

In the case of a butadiene (BD) selective hydrogenation reactor, operation can be conducted in either the liquid or vapor phase. In the case of liquid phase operation, the inlet operating temperature may range from about 20 to about 120° C., such as from about 40 to about 100° C. Representative operating pressures may range from about 150 psig to about 600 psig (about 1000 to 4100 kPa), such as from about 200 psig to about 400 psig (about 1400 to 2800 kPa). The LHSV may range from about 0.1 to about 100, such as from about 1 to about 25. In the case of the vapor phase operation, the inlet operating temperature may range from about 20 to about 600° C., such as from about 50 to about 200° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, preferably from about 1 to about 10. The feedstreams in BD selective hydrogenation processes may contain at least 90% butylene, and greater than 0.2% butadiene.

The invention will now be more particularly described with reference to the following Examples.

EXAMPLE 1 (CONTROL)

0.4 wt % Rh, 0.8 wt % In, 0.8 wt % Fe on $Al_2O_3$ 40 gm of theta-alumina (SBa-90 supplied by Sasol) were mixed with 100 ml de-ionized water to produce a slurry. Then 2.32 gm $Fe(NO_3)_3.9H_2O$ (supplied by Aldrich) were dissolved in 40 ml de-ionized water and the resulting solution was added to the alumina slurry. After 1 hour stirring, the slurry was gently heated until most of the water was removed. The resulting paste was dried in an oven for 2 hours at 90° C. The remaining powder was calcined under air for 2 hours at 120° C. and 4 hours at 400° C.

The following day, 10 gm of the Fe-impregnated alumina were mixed with 40 ml de-ionized water to produce a slurry. Then 0.13 gm $Rh(NO_3)_3.2H_2O$ (supplied by Alfa Aesar) and 0.21 gm $In(NO_3)_3.2H_2O$ (supplied by Alfa Aesar) were dissolved in 80 ml de-ionized water and the resulting bimetallic solution was added to the slurry. After 1 hour stirring, the slurry was gently heated until most of the water was removed. The resulting paste was dried in an oven for 2 hours at 90° C. The remaining powder was calcined under air for 2 hours at 120° C. and 4 hours at 400° C. The resulting catalyst was designated Catalyst A.

EXAMPLE 2 (INVENTION)

0.4 wt % Rh, 0.8 wt % In, 0.8 wt % Fe on $Al_2O_3$ 40 gm of theta-alumina (SBa-90 supplied by Sasol) were mixed with 100 ml de-ionized water to produce a slurry.

Then 2.32 gm $Fe(NO_3)_3 \cdot 9H_2O$ (supplied by Aldrich) were dissolved in 40 ml de-ionized water and the resulting solution was added to the alumina slurry. After 1 hour stirring, the slurry was gently heated until most of the water was removed. The resulting paste was dried in an oven for 2 hours at 90° C. The remaining powder was calcined under air for 2 hours at 120° C. and 4 hours at 400° C.

The following day, 10 gm of the Fe-impregnated alumina were mixed with 40 ml de-ionized water to produce a slurry. Then 0.28 gm 2-amino-2-methyl-1-propanol (supplied by Avocado) was added to the slurry. Thereafter 0.13 gm $Rh(NO_3)_3 \cdot 2H_2O$ (supplied by Alfa Aesar) and 0.21 gm $In(NO_3)_3 \cdot 2H_2O$ (supplied by Alfa Aesar) were dissolved in 80 ml de-ionized water and the resulting bimetallic solution was added to the slurry. After 1 hour stirring, the slurry was gently heated until most of the water was removed. The resulting paste was dried in an oven for 2 hours at 90° C. The remaining powder was calcined under air for 2 hours at 120° C. and 4 hours at 400° C. The resulting catalyst was designated Catalyst B.

EXAMPLE 3 (CONTROL)

0.4 wt % Rh, 0.4 wt % In, 4.8 wt % Fe on $Al_2O_3$ 40 gm of theta-alumina (supplied by Sud Chemie, 2–4 mm spheres) were weighed and set in a beaker. Then 13.92 gm $Fe(NO_3)_3 \cdot 9H_2O$ (supplied by Aldrich) were dissolved in 15 ml de-ionized water and the resulting iron solution was sprayed onto the alumina spheres. The spheres were dried in an oven for 6 hours at 80° C., and then calcined under air for 2 hours at 120° C. and 4 hours at 450° C.

The following day, 20 gm of the Fe-impregnated alumina spheres were loaded in a 500 ml flask and mixed with 40 ml de-ionized water. The flask was mounted on a rotary evaporator and the spheres were stirred for a few minutes. Meanwhile 0.26 gm $Rh(NO_3)_3 \cdot 2H_2O$ (supplied by Alfa Aesar) and 0.21 gm $In(NO_3)_3 \cdot 2H_2O$ (supplied by Alfa Aesar) were dissolved in 80 ml de-ionized water and the resulting bimetallic solution was poured into the flask containing the spheres. After 1 hour stirring, the water was slowly evaporated under vacuum. The spheres were then dried in an oven for 6 hours at 80° C., and finally calcined under air for 2 hours at 120° C. and 4 hours at 450° C. The resulting catalyst was designated Catalyst C.

EXAMPLE 4 (INVENTION)

0.4 wt % Rh, 0.4 wt % In, 4.8 wt % Fe on $Al_2O_3$ 40 gm of theta-alumina (supplied by Sud Chemie, 2–4 mm spheres) were weighed and set in a beaker. Then 13.92 gm $Fe(NO_3)_3 \cdot 9H_2O$ (supplied by Aldrich) were dissolved in 15 ml de-ionized water and the resulting iron solution was sprayed onto the alumina spheres. The spheres were dried in an oven for 6 hours at 80° C., and then calcined under air for 2 hours at 120° C. and 4 hours at 450° C.

The following day, 20 gm of the Fe-impregnated alumina spheres were loaded in a 500 ml flask and mixed with 40 ml de-ionized water. Then 0.56 gm 2-amino-2-methyl-1-propanol (supplied by Avocado) was poured into the flask. The flask was mounted on a rotary evaporator and the spheres were stirred for a few minutes. Meanwhile 0.26 gm $Rh(NO_3)_3 \cdot 2H_2O$ (supplied by Alfa Aesar) and 0.21 gn $In(NO_3)_3 \cdot 2H_2O$ (supplied by Alfa Aesar) were dissolved in 80 ml de-ionized water and the resulting bimetallic solution was poured into the flask containing the spheres. After 1 hour stirring, the water was slowly evaporated under vacuum. The spheres were then dried in an oven for 6 hours at 80° C., and finally calcined under air for 2 hours at 120° C. and 4 hours at 450° C. The resulting catalyst was designated Catalyst D.

EXAMPLE 5

This Example shows the influence of the organic aid on the ethylene selectivity of the catalysts of Examples 1 and 2.

In each case, the catalysts were prereduced at 450° C. for 4 hours under a 100% hydrogen atmosphere and were then evaluated under the following conditions: temperature=100° C., pressure=300 psig, GHSV=4500, $H_2/C_2H_2$ feed ratio=1.05, time on stream=14 hours. The hydrocarbon feed contained nominally 1.65 mole % acetylene and 70 mole % ethylene, with balance being nitrogen. Test results are given in Table 1 below.

TABLE 1

| Catalyst | $C_2H_2$ conv (%) | $H_2$ conv. (%) | $C_2H_4$ select (%) | Green Oil select (%) |
|---|---|---|---|---|
| B | 97.6 | 100 | 79.1 | 4.7 |
| A | 77.3 | 100 | 45.9 | 6.0 |

It will be seen that catalyst B (employing the organic aid in the second impregnation step) had a significantly higher ethylene selectivity than the identical catalyst A (but without the organic aid in the second impregnation step) under the same test conditions. Since the $H_2/C_2H_2$ ratio is 1.05 and the $H_2$ conversion is 100% in both cases, the greater ethylene selectivity results in a greater acetylene conversion with catalyst B.

EXAMPLE 6

Catalysts C and D were prereduced at 480° C. for 5 hours under a 100% hydrogen atmosphere and were then evaluated under the following conditions: temperature=100° C., pressure=300 psig, GHSV=4500, $H_2/C_2H_2$ feed ratio=1.05, time on stream=4 hours. Again, the hydrocarbon feed contained nominally 1.65 mole % acetylene and 70 mole % ethylene, with balance being nitrogen. Test results are given in Table 2 below.

TABLE 2

| Catalyst | $C_2H_2$ conv (%) | $H_2$ conv. (%) | $C_2H_4$ select (%) | Green Oil select (%) |
|---|---|---|---|---|
| D | 73.7 | 80.4 | 71 | 4.8 |
| C | 78.7 | 100 | 48.5 | 9.7 |

Although the use of spheres rather powder as the catalyst support led to some activity loss, again it will be seen that the catalyst employing the organic aid during the second impregnation step, Catalyst D, had a higher ethylene selectivity. In addition, catalyst D had a lower green oil selectivity than the catalyst produced without the organic aid, catalyst C.

While the present invention has been described and illustrated by reference to particular embodiments, those of ordinary skill in the art will appreciate that the invention lends itself to variations not necessarily illustrated herein. For this reason, reference should be made solely to the appended claims for purposes of determining the true scope of the present invention.

The invention claimed is:

1. A process for selectively removing alkynes and/or diolefins from a feedstock also containing olefins, the process comprising contacting the feedstock with hydrogen in the presence of a catalyst composition comprising a support and at least one metal component selected from Groups 8 to 10 of the Periodic Table of Elements, wherein the catalyst composition is produced by a method comprising:
   (a) impregnating the support with a compound of said at least one metal;
   (b) contacting said support with at least one organic nitrogen-containing compound; and
   (c) calcining the support.

2. The process of claim 1 wherein contacting said support with said at least one organic nitrogen-containing compound is effected before impregnation of the support with said compound of said at least one metal.

3. The process of claim 1 wherein contacting said support with said at least one organic nitrogen-containing compound is effected after impregnation of the support with said compound of said at least one metal.

4. The process of claim 1 wherein contacting said support with said at least one organic nitrogen-containing compound is effected during impregnation of the support with said compound of said at least one metal.

5. The process of claim 1 wherein said at least one metal selected from Groups 8 to 10 of the Periodic Table of Elements includes rhodium.

6. The process of claim 5 wherein the catalyst composition further comprises at least one metal component selected from Group 13 of the Periodic Table of Elements.

7. The process of claim 6 wherein said at least one metal component selected from Group 13 of the Periodic Table of Elements includes indium.

8. The process of claim 7 wherein the catalyst composition includes at least one additional metal component different from rhodium and selected from Groups 8 to 10 of the Periodic Table of Elements.

9. The process of claim 7 wherein the catalyst composition includes at least one additional metal component selected from iron, ruthenium and cobalt.

10. The process of claim 9 wherein said at least one additional metal component is impregnated on said support before the impregnation of said compound of said at least one metal.

11. The process of claim 10 wherein contacting said support with said at least one organic nitrogen-containing compound is effected after impregnation of said support with said at least one additional metal component.

12. The process of claim 1 wherein said support is selected from alumina, zirconia and ceria/alumina.

13. The process of claim 1 wherein said organic nitrogen-containing compound is an aminoacid or an aminoalcohol.

14. The process of claim 1 wherein said organic nitrogen-containing compound is an aminoalcohol.

15. The process of claim 1 wherein said organic nitrogen-containing compound is 2-amino-2-methyl-1-propanol.

16. The process of claim 1 wherein said calcining (c) is effected at a temperature of about 100° C. to about 650° C.

17. The process of claim 1 wherein the alkynes and/or diolefins have 2 to 4 carbon atoms and the feedstock also contains $C_2$ to $C_4$ olefins.

18. The process of claim 1 wherein contacting said feedstock with hydrogen the presence of said catalyst composition is conducted at a temperature of from about 20° C. to about 150° C., a pressure of from about 690 kPa to 4100 kPa, and a molar ratio of hydrogen to ailcynes and/or diolefins of from about 1 to about 1000.

* * * * *